United States Patent [19]  [11] 4,439,444
Nisato et al. [45] Mar. 27, 1984

[54] AMIDOBENZAMIDES, THEIR SALTS AND PHARMACEUTICAL COMPOSITIONS CONTAINING THEM

[75] Inventors: Dino Nisato, Pavia; Sergio Boveri, Tortona; Alberto Bianchetti, Milan, all of Italy; Romeo Roncucci, Paris, France; Paolo Carminati, Milan, Italy

[73] Assignee: Sanofi, Paris, France

[21] Appl. No.: 396,100

[22] Filed: Jul. 7, 1982

[30] Foreign Application Priority Data

Jul. 8, 1981 [FR] France ................... 81 13420
Oct. 23, 1981 [FR] France ................... 81 19967
Dec. 10, 1981 [FR] France ................... 81 23084

[51] Int. Cl.³ ................ A61K 31/34; C07D 307/54
[52] U.S. Cl. .................. 424/285; 424/250; 424/263; 424/266; 544/405; 546/283; 549/494
[58] Field of Search ............. 549/494; 544/405; 546/283; 424/250, 263, 266, 285

[56] References Cited

U.S. PATENT DOCUMENTS 4,318,858  3/1982  Hirai et al. ................... 549/494

FOREIGN PATENT DOCUMENTS 2003471  3/1979  United Kingdom .
2065644  7/1981  United Kingdom .

*Primary Examiner*—Richard Raymond
*Attorney, Agent, or Firm*—Weingarten, Schurgin, Gagnebin & Hayes

[57] ABSTRACT

Amidobenzamides acting as histamine $H_2$ receptors blocking agents, of formula

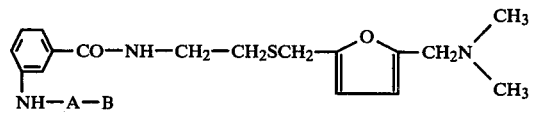

wherein A is CO or $SO_2$ and B is alkyl, phenyl, pyridyl, pyridyl-1-oxyde, pyrazinyl or thienyl; their salts; process for their preparation by reaching 2-(5-dimethyl-aminomethylfuran-2-ylmethylthio)ethylamine with a derivative of formula

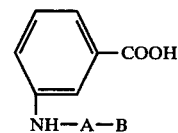

and optional salification and pharmaceutical compositions containing same.

6 Claims, No Drawings

AMIDOBENZAMIDES, THEIR SALTS AND PHARMACEUTICAL COMPOSITIONS CONTAINING THEM

The present invention relates to novel amidobenzamides having a histamine $H_2$ receptor blocking activity, to their salts, to a process for their preparation and to pharmaceutical compositions containing them as active ingredients.

After the subdivision of histamine receptors into $H_1$ receptors (Ash and Schild, Brit. J. Pharmac. Chemother. 1966, 27, 427) and $H_2$ receptors (Black et al., Nature 1972, 236, 335) and the discovery that the selective block of the $H_2$ receptors induces an inhibition of the gastric secretion, many products have been proposed as antagonists of the histamine $H_2$ receptors, hereinafter referred to as "$H_2$blockers". Thus, the compounds having received the International Non-proprietary Names burimamide, metiamide, cimetidine, ranitidine, tiotidine, etintidine, oxmetidine have formed the subject matter of a large number of scientific publications and one of them, cimetidine, already constitutes a tool in the doctor's hand for the treatment of the ulcerous disease.

All of the above-mentioned products are characterised by the presence in their molecule of the following structure:

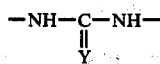   I wherein Y represents an oxygen or sulfur atom or an N—CN or CH—NO$_2$ group, said structure being linear or included in a cycle as in the case of oxmetidine. The above-mentioned products are therefore all characterised by the presence of two geminal nitrogen atoms on a carbon atom.

The French Patent Application No. 2 471 376 describes and claims benzamides of formula

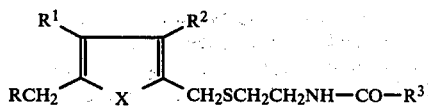   II wherein R is the dimethylamino or 1-pyrrolidinyl group; $R^1$ and $R^2$ are each hydrogen or an alkyl group of from 1 to 3 carbon atoms; $R^3$ is hydrogen, an alkyl group of from 1 to 3 carbon atoms (optionally substituted by a member selected from the group consisting of cyano, alkoxy of from 1 to 3 carbon atoms, phenyl and pentagonal or hexagonal heterocyclic groups), a cycloalkyl group of from 3 to 6 carbon atoms, an alkenyl group of from 2 to 5 carbon atoms (optionally substituted by a member selected from the group consisting of alkoxy of from 1 to 3 carbon atoms, phenyl and phenoxy groups), an aryl group of from 6 to 10 carbon atoms (optionally substituted by one or two members selected from the group consisting of hydroxy, halogen, nitro, sulfamoyl, alkyl of from 1 to 3 carbon atoms, alkoxy of from 1 to 3 carbon atoms, alkanoyl of from 1 to 3 carbon atoms, alkoxycarbonyl of from 2 to 4 carbon atoms, dialkylamino of from 2 to 4 carbon atoms and alkanesulfonyl of from 1 to 3 carbon atoms), or a pentagonal or hexagonal heterocyclic group (eventually substituted by a member selected from the group consisting of oxo, halogen, alkyl of from 1 to 3 carbon atoms and alkoxy of from 1 to 3 carbon atoms) and X is oxygen or sulfur, as well as their pharmaceutically acceptable acid addition salts.

Among the compounds described in the above-mentioned patent, the compound of formula II where R=dimethylamino, $R^1=R^2=H$, and $R^3=$4-sulfamoylphenyl, namely the N-[2-(5-dimethylaminomethylfuran-2-ylmethylthio)ethyl]-4-sulfamoylbenzamide, as oxalate, shows an ED$_{50}$ of 2.54 mg/kg in the gastric acid secretion inhibiting activity in the rat.

The above French patent application, which provides compounds not having the structure I, in its general formula doesn't include any amidobenzamide, namely any benzamide substituted in the benzene ring by an acylamido or sulfonylamido group.

It is also known that histamine $H_2$ receptors are located not only in the gastric mucous membrane but also in the sinusal node, in the ventricular myocardium and in the coronary vessels and that the known $H_2$ blockers are active both on the cardiac and gastric receptors. Thus, the block of the cardiac $H_2$ receptors may be the cause of the bradycardia and of the asystolia observed as side effects in the treatment of the ulcerous disease by cimetidine (Clinica Terapeutica, 1981, 96, 81-91, in particular page 84).

It is therefore desiderable to have available compounds which present a dissociation between the gastric and cardiac $H_2$ receptor blocking activities, in favour of the former, which are further capable of giving lower side effects at cardiac level.

It has now been found that certain novel amidobenzamides, not having the structure I hereinabove, have a good action antagonising the histamine $H_2$ receptors and that this action is preferably directed towards the gastric receptors.

It has also surprisingly been found that the $H_2$ blocking action occurs at a satisfactory level only when the "amido" group is in the meta position of the benzamide phenyl ring.

It has also been found that said novel amidobenzamides don't present the characteristical side effects of the compounds with $H_2$ blocking activity, particularly cimetidine, such as the anti-andromyogenic effect.

Thus, according to one of its aspects, it is an object of the present invention to provide novel amidobenzamides of formula

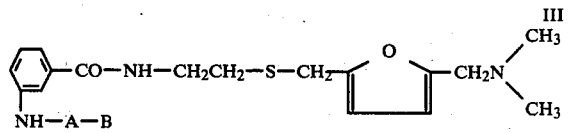   III wherein A represents a CO or SO$_2$ group and B represents an alkyl group of from 1 to 6 carbon atoms or a phenyl, pyridyl, pyridyl 1-oxyde, pyrazinyl or thienyl group, as well as their pharmaceutically acceptable salts.

The pharmaceutically acceptable salts include the non-toxic salts derived from mineral or organic acids salifying one or the two basic functions present in the molecule of the compounds of formula III, such as hydrochloride, hydrobromide, sulfate, succinate, tartrate, citrate, fumarate, maleate, 4,4'-methylene-bis-(3-hydroxy-2-naphtoate), hereinafter referred to as "pamoate", 2-naphtalene-sulfonate, hereinafter referred to as "napsylate", methanesulfonate, hereinafter referred to as "mesylate", p-toluenesulfonate, hereinafter referred to as "tosylate", and the like.

According to another of its aspects, the present invention relates to a process for the preparation of compounds of formula III above, said process comprising treating the 2-(5-dimethylaminomethylfuran-2-ylmethylthio)ethylamine of formula

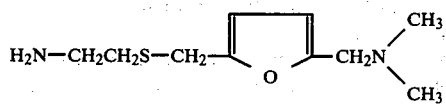

with a functional derivative of the benzoic acid of formula

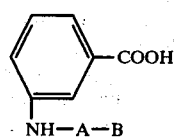

wherein A and B are as hereinabove defined, in an organic solvent at a temperature between 0° C. and the boiling temperature of the solvent employed. The compound thus obtained may be converted into its pharmaceutically acceptable salts.

The anhydride, a mixed anhydride, the chloride or an active ester may be used as a suitable functional derivative.

A preferred functional derivative of the acid of formula V above is represented by the following formula

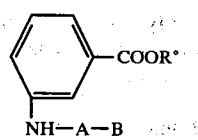

wherein A and B are as hereinbefore defined and R° represents a nitrophenyl, methoxyphenyl, trityl or benzhydryl group.

The reaction temperature may vary between 0° C. and the boiling point of the solvent employed, but the operation is generally carried out at room temperature or at 30°-50° C. It may be preferable to carry out the reaction in the cold when it is exothermic, as in the case of the chloride being used as a functional derivative of the benzoic acid of formula V.

An alcohol, such as methanol or ethanol, or a halogenated solvent, such as methylene chloride, dichloroethane, chloroform and the like, is preferably used as a reaction solvent, but other organic solvents compatible with the reagents employed, for example dioxan, tetrahydrofuran or a hydrocarbon such as hexane may also be used.

The reaction may be carried out in the presence of a proton acceptor, for example an alkaline carbonate or a tertiary amine, when hydrochloric acid, or another acid, forms during the reaction, but this proton acceptor is not indispensable for obtaining the final product.

The reaction is fairly rapid; after 2-4 hours at room temperature or at 30°-50° C. the reaction is generally over and the amidobenzamide of formula III obtained is isolated according to conventional techniques in the form of free base or of one of its salts.

The free base may be converted into one of its pharmaceutically acceptable salts by treatment with a solution of the suitable acid in an organic solvent. If the amidobenzamide III is isolated as a salt, the corresponding free base can be splitted off with an alcaline hydroxide or carbonate.

The novel compounds of formula III of the present invention, as well as their pharmaceutically acceptable salts, act as selective antagonists of the histamine $H_2$ receptors by selectively inhibiting the gastric secretion at gastric $H_2$ receptor level with slight activity on the cardiac $H_2$ receptors and are therefore useful for the treatment of the ulcerous disease.

The selective activity of the products of the present invention towards the receptors of type $H_2$ is confirmed by the absence of activity of type $H_1$ in the test of the contraction induced by histamine on the isolated guinea pig ileum.

The antagonistic activity of the amidobenzamides of the present invention towards the gastric histamine $H_2$ receptors was confirmed in the test of the antisecretory activity based on the antagonism for the hypersecretion induced by histamine in rat according to the method of Ghosh and Schild (Brit. J. Pharmacol. 1958, 13, 54). According to this test, a gastric acid hypersecretion is induced by intravenous infusion of a sub-maximal dose of histamine equivalent to 15 mcmol/kg/hour and the gastric secretion is measured by perfusion of a physiological solution at a constant speed in the stomach of the animal.

Table I shows, for the representative compounds of the present invention, indicated by their code numbers, and for three reference compounds, namely 2-cyano-1-methyl-3-[2[(5-methylimidazol-4-yl)methylthio]ethyl]-guanidine, hereinafter designated by its International Non-proprietary Name "cimetidine", N-[2[[5-[(dimethylamino)methyl]furfuryl]thio]ethyl]-N'-methyl-2-nitro-1,1-ethenediamine, hereinafter designated by its International Non-proprietary Name "ranitidine" and N-[2-(5-dimethylaminomethylfuran-2-ylmethylthio)ethyl]-4-sulfamoyl benzamide, described in the above-mentioned Patent Application FR 2 471 376, hereinafter designated "Compound A", the dose (in mcmol/kg by intravenous route in a single administration) which inhibits by 50% the gastric hypersecretion induced by histamine ($ID_{50}$). Such a $ID_{50}$ represents the index of the gastric $H_2$ blocking action.

TABLE I

| Compound | $ID_{50}$ (mcmol/kg) | Relative potency (cimetidine = 1) |
|---|---|---|
| Cimetidine | 0.95 | 1.00 |
| Ranitidine | 0.25 | 3.80 |
| Compound A | 2.26 | 0.42 |
| CM 57822 | 0.98 | 0.97 |
| CM 57888 | 0.63 | 1.50 |
| SR 57912 | 0.33 | 2.88 |
| SR 57922 | 1.15 | 0.82 |
| SR 57927 A | 1.15 | 0.82 |
| SR 57933 | 1.82 | 0.52 |
| SR 57975 | 0.93 | 1.02 |
| SR 57981 A | 0.49 | 1.94 |

It results form this table that all the representative compounds of the present invention are more active than Compound A and that most of them have an activity comparable with or superior to that of cimetidine.

Two products, namely SR 57981 A and SR 57912 are very powerful and the activity of the latter is very close to that of ranitidine.

The antagonistic activity of the compounds of the present invention towards the cardiac histamine $H_2$ receptors has been assessed in the test of the inhibition of the increase in the frequency induced by histamine on the right atrium of the guinea pig (D. Reinhardt et al., Agents and Actions 1974, 4; 217-221).

Table II shows, for four representative compounds of the present invention, designated by their code numbers CM 57822, CM 57888, SR 57912 and SR 57922 as well as for cimetidine, ranitidine and Compound A, the concentration of product under examination which inhibits by 50% the increase in the frequency induced by histamine on the isolated right atrium of the guinea pig ($IC_{50}$). Such an $IC_{50}$ represents the index of cardiac $H_2$ blocking action.

TABLE II

| Compound | $IC_{50}$ mcmol/kg | Relative potency (cimetidine = 1) |
| --- | --- | --- |
| Cimetidine | $4 \cdot 10^{-7}$ | 1 |
| Ranitidine | $8 \cdot 10^{-8}$ | 5 |
| Compound A | $3.1 \cdot 10^{-7}$ | 1.3 |
| CM 57822 | $2 \cdot 10^{-6}$ | 0.2 |
| CM 57888 | $5.9 \cdot 10^{-7}$ | 0.67 |
| SR 57912 | $5 \cdot 10^{-6}$ | 0.08 |
| SR 57922 | $6 \cdot 10^{-6}$ | 0.06 |

It results from this table that all the representative compounds of the present invention are less active than cimetidine as cardiac $H_2$ blocking agents, whilst Compound A is more active.

Thus, the compounds of the present invention, in comparison with the products of the prior art, show a good dissociation between cardiac and gastric $H_2$ blocking activities in favour of the latter.

The anti-andromyogenic effect of a representative compound of the present invention, namely CM 57888, has been assessed in comparison with cimetidine and ranitidine in immature Sprague Dawley rats (9 each lot) of CD (SD) BR (Charles River-France) strain, castrated at the age of 22-23 days and whose genitals as well as the levator ani muscle have been stimulated by a daily injection of testosterone.

Testosterone was administered by sub-cutaneous route, suspended in a vehicle for steroids, both at the dose of 0.2 mg/animal/day, and 0.4 mg/animal/day. For each dose of testosterone, cimetidine, ranitidine and CM 57888 were simultaneously injected by intraperitoneal route, in saline, in the case of ranitidine and suspended in a vehicle for steroids for the two other substances; the administered doses were 400 mg/kg/day for cimetidine, 100 mg/kg/day for ranitidine and 200 mg/kg/day for CM 57888. As a control it was used a lot of animals treated with the vehicles only. The treatment lasted 8 days. The animals were killed 24 hours after the last injection, the ventral prostrate, the seminal vescicles and the levator ani were immediately drawn and weighed.

It has been found that the three substances show an anti-androgenic and anti-anabolising activity. However, at the employed doses, the activity of CM 57888 was much lower than that of the reference compounds since, contrary to them, the representative compound of the invention did not exhibit any effect when testosterone was administered at the dose of 0.4 mg/animal/day. This experiment shows that the compound of the present invention has a reduced possibility of giving the characteristical side effects connected with the anti-andromyogenic acitivity of the known $H_2$ blockers.

With respect to their degree of activity, the compounds of the present invention are scarcely toxic and present a good therapeutic index.

Thus, according to another of its aspects, the present invention relates to pharmaceutical compositions containing, as active ingredients, the amidobenzamides of formula III above, as well as their pharmaceutically acceptable addition salts.

In the pharmaceutical compositions with $H_2$ blocking activity according to the present invention, for oral, sublingual, sub-cutaneous, intramuscular, intravenous, transdermic or rectal administration, the active ingredients can be administered in unit forms of administration, with conventional pharmaceutical carriers, to animals and human beings in the treatment of gastric hypersecretion and peptic ulcers.

In order to obtain the desired $H_2$ blocking effect, the daily dose of active ingredient may vary between 1 and 100 mg per kg of body weight, preferably from 10 to 50 mg/kg.

Each unit dose may contain from 10 to 1000 mg (preferably from 100 to 500 mg) of active ingredient in combination with a pharmaceutical carrier. This unit dose may be administered 1 to 4 times daily.

Among the appropriate unit forms of administration, there are tablets, capsules, powders, granules and oral solutions or suspensions and the forms for sublingual administration, suppositories as well as the forms for parenteral administration.

When a solid composition is prepared in the form of tablets, the main active ingredient is mixed with a pharmaceutical excipient such as gelatine, starch, lactose, magnesium stearate, talc, arabic gum and the like. The tablets may be coated with sucrose or other appropriate materials or they may be treated so that their activity is extended or delayed and that they continually release a predetermined amount of active ingredient.

A preparation in capsules is obtained by mixing the active ingredient with a diluent and by pouring the mixture obtained in soft or hard capsules.

A preparation in the form of syrup or elixir may contain the active ingredient jointly with a possibly acaloric sweetening agent, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents.

For rectal applications, suppositories are prepared with binding agents melting at rectal temperature, for example, cocoa butter or polyethyleneglycols.

For parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules, possibly with one or more supports or additives.

The following examples illustrate the invention without, however, limiting its scope.

EXAMPLE 1

A mixture of 4.3 g (0.02 mole) of 2-(5-dimethylaminomethylfuran-2-ylmethylthio)ethylamine and 6 g (0.02 mole) of 4-nitrophenyl 3-acetamidobenzoate in 150 ml of methanol is stirred at 40° C. for 2.5 hours. The solvent is evaporated under reduced pressure and the residue is taken up with 100 ml of N hydrochloric acid. The acid solution is washed twice with 40 ml of ethyl acetate and the pH is adjusted to 7.8 with sodium hydroxide. The product is thoroughly extracted with ethyl acetate, the organic phase is dried over anhydrous sodium sulfate and the solvent is evaporated under reduced pressure. The residue is dissolved in 20 ml of isopropanol and the solution thus obtained is poured into a solution of 1.7 g of anhydrous oxalic acid in 20 ml of isopropanol. The precipitate is filtered and crystallized from ethanol. Thus, 6 g of 3-acetamido-N-[2-(5-dimethylaminomethylfuran-2-ylmethylthio)ethyl]benzamide oxalate, designated by its code number CM 57820, are obtained; m.p. 123°–126° C.

In the same manner, by reacting 0.02 mole of 2-(5-dimethylaminomethylfuran-2-ylmethylthio)ethylamine with 0.02 mole of 4-nitrophenyl 3-proprionamidobenzoate, with 0.02 mole of 4-nitrophenyl 3-butyramidobenzoate and, respectively, with 0.02 mole of 4-nitrophenyl 3-trimethylacetamidobenzoate:
the 3-propionamido-N-[2-(5-dimethylaminomethylfuran-2-ylmethylthio)ethyl]benzamide oxalate; m.p. 133°–135° C.;
the 3-butyramido-N-[2-(5-dimethylaminomethylfuran-2-ylmethylthio)ethyl]benzamide oxalate; m.p. 125°–127° C.; and, respectively,
the 3-trimethylacetamido-N-[2-(5-dimethylaminomethylfuran-2-ylmethylthio)ethyl]benzamide oxalate; m.p. 153°–155° C., are obtained.

EXAMPLE 2

A solution of 0.02 mole of 2-(5-dimethylaminomethylfuran-2-ylmethylthio)ethylamine and 0.02 mole of 4-nitrophenyl 3-methanesulfonamidobenzoate in 150 ml of methanol is heated at 45° C. under stirring for 2 hours. The solvent is evaporated under reduced pressure and the residue is taken up with 100 ml of N hydrochloric acid. The acid solution is washed with ethyl acetate and the pH is adjusted to 7.5 with sodium hydroxide. The product is thoroughly extracted with ethyl acetate, the organic phase is dried over anhydrous sodium sulfate, the solvent is evaporated under reduced pressure and the residue is dissolved in 20 ml of warm isopropanol. The 3-methanesulfonamido-N-[2-(5-dimethylaminomethylfuran-2-ylmethylthio) ethyl]benzamide, designated by its code number CM 57822, is thus obtained. After crystallization from isopropanol, it melts at 109°–111° C.

In the same manner, by reacting 0.02 mole of 2-(5-dimethylaminomethylfuran-2-ylmethylthio)ethylamine with 0.02 mole of 4-nitrophenyl 3-ethanesulfonamidobenzoate and, respectively, with 0.02 mole of 4-nitrophenyl 3-butanesulfonamidobenzoate, there is obtained
the 3-ethanesulfonamido-N-[2-(5-dimethylaminomethylfuran-2-ylmethylthio)ethyl]benzamide and, respectively,
the 3-butanesulfonamido-N-[2-(5-dimethylaminomethylfuran-2-ylmethylthio)ethyl]benzamide, isolated as oxalate as described in Example 1, SR 57981 A; m.p. 103°–110° C.

EXAMPLE 3

To a suspension of 0.05 mole of 3-benzenesulfonamidobenzoic acid and 0.05 mole of 4-nitrophenol in 250 ml of anhydrous methylene chloride, 0.05 mole of dicyclohexylcarbodiimide is added. The mixture is refluxed for 4 hours, then evaporated under reduced pressure. The residue is taken up with 300 ml of methanol and to the solution thus obtained 0.05 mole of 2-(5-dimethylaminomethylfuran-2-ylmethylthio)ethylamine is added. The reaction mixture is refluxed for 2 hours, then evaporated under reduced pressure to dryness. The residue is thoroughly taken up with 150 ml of N hydrochloric acid and 100 ml of ethyl acetate and then filtered off. The organic layer is separated, the aqueous layer is adjusted to pH 7.8 and thoroughly extracted with ethyl acetate. The organic phases are collected, dried over anhydrous sodium sulfate and evaporated under reduce pressure. The residue is taken up with 40 ml of isopropanol and 9.1 g of 3-benzenesulfonamido-N-[2-(5-dimethylaminomethylfuran-2-ylmethylthio)ethyl]benzamide, CM 57888, are thus obtained; after crystallization from isopropanol the product melts at 119°–121° C.

In the same manner, 0.05 mole of 3-(3-pyridinesulfonamido)benzoic acid and, respectively of 3-(2-thiophenesulfonamido)benzoic acid are reacted with 0.05 mole of 4-nitrophenol in 250 ml of anhydrous methylene chloride in the presence of 0.05 mole of dicyclohexylcarbodiimide. The active ester thus obtained is treated with 0.05 mole of 2-(5-dimethylaminomethylfuran-2-ylmethylthio)ethylamine. Thus,
the 3-(3-pyridinesulfonamido)-N-[2-(5-dimethylaminomethylfuran-2-ylmethylthio)ethyl]benzamide, SR 57933, in the form of a vitreous solid isolated from diethyl ether; m.p. 80°–83° C. (dec.) and, respectively,
the 3-(2-thiophenesulfonamido)-N-[2-(5-dimethylaminomethylfuran-2-ylmethylthio)ethyl]benzamide, SR 57975, crystallized from ethyl acetate, m.p. 113°–115° C., are obtained.

EXAMPLE 4

By operating as described in Examples 1–3, by reacting 0.02 mole of 2-(5-dimethylaminomethylfuran-2-ylmethylthio)ethylamine with the active ester obtained from 0.02 mole of 3-benzamidobenzoic acid and 0.02 mole of 4-nitrophenol in the presence of dicyclohexylcarbodiimide, the 3-benzamido-N-[2-(5-dimethylaminomethylfuran-2-ylmethytlhio)ethyl]benzamide, SR 57916, is obtained. After crystallization from ethyl acetate, it melts at 112°–115° C.

Similarly, by reacting 2-(5-dimethylaminomethylfuran-2-ylmethylthio)ethylamine with, respectively, the active ester of 3-(2-thienylcarboxamido)benzoic acid, 3-(3-pyridinecarboxamido)benzoic acid, 3-(4-pyridinecarboxamido)benzoic acid, 3-(2-pyridinecarboxamido)benzoic acid and 3-(2-pyrazinecarboxamido)benzoic acid,
the 3-(2-thienylcarboxamido)-N-[2-(5-dimethylaminomethylfuran-2-ylmethylthio)ethyl]benzamide, SR 57922, m.p. 116°–118° C.;
the 3-(3-pyridinecarboxamido)-N-[2-(5-dimethylaminomethylfuran-2-ylmethylthio)ethyl]benzamide dioxalate, SR 57927 A, crystallized from 95% ethanol, m.p. 137°–140° C.;
the 3-(4-pyridinecarboxamido)-N-[2-(5-dimethylaminomethylfuran-2-ylmethylthio)ethyl]benzamide dioxalate, SR 57944 A, crystallized from 95% ethanol, m.p. 176°–178° C.;

the 3-(2-pyridinecarboxamido)-N-[2-(5-dimethylaminomethylfuran-2-ylmethylthio)ethyl]benzamide oxalate, SR 57953 A, crystallized from ethanol, m.p. 143°–145° C.; and the 3-(2-pyrazinecarboxamido)-N-[2-(5-dimethylaminomethylfuran-2-ylmethylthio)ethyl]benzamide, SR 57939, m.p. 80°–82° C., are obtained.

EXAMPLE 5

To a suspension of 9.5 g (0.037 mole) of 3-[(3-pyridine 1-oxyde)carboxamido]benzoic acid and 5 g (0.037 mole) of 4-nitrophenol in 400 ml of anhydrous methylene chloride, 7.7 g (0.037 mole) of dicyclohexylcarbodiimide are added. The mixture is heated at reflux for 4 hours, then evaporated under reduced pressure. The residue is taken up with 300 ml of methanol and, to the solution thus obtained, 7.9 g (0.037 mole) of 2-(5-dimethylaminomethylfuran-2-ylmethylthio)ethylamine are added. The reaction mixture is heated at 40° C. for 2.5 hours and evaporated to dryness under reduced pressure. The residue is thoroughly taken up with 70 ml of water and hydrochloric acid to a strong acidic pH, then the solution is washed with a mixture ethyl acetate:ethanol 9:1. The organic phases are collected, dried over anhydrous sodium sulfate and evaporated under reduced pressure to dryness. The residue is taken up with 10 ml acetone. Thus, 0.3 g of 3-[(3-pyridine 1-oxyde)carboxamido]-N-[2-(5-dimethylaminomethylfuran-2-ylmethylthio)ethyl]benzamide, designated by its code number SR 57912, are obtained; m.p. 160°–162° C.

In the same manner, by reacting 0.037 mole of 2-(5-dimethylaminomethylfuran-2-ylmethylthio)ethylamine with the active ester obtained from 0.037 mole of 3-[(4-pyridine 1-oxyde)carboxamido]benzoic acid and 0.037 mole of 4-nitrophenol in the presence of dicyclohexylcarbodiimide, the 3-[(4-pyridine 1-oxyde)carboxamido]-N-[2-(5-dimethylaminomethylfuran-2-ylmethylthio)-ethyl]benzamide, SR 57937, is obtained which, after crystallization from isopropanol, melts at 145°–147° C.

EXAMPLE 6

To a solution of 1 g of 3-benzenesulfonamido-N-[2-(5-dimethylaminomethylfuran-2-ylmethylthio)ethyl]benzamide in 15 ml of ethanol, a solution of 0.3 g of oxalic acid in 10 ml of ethanol is added. The salt which precipitates is filtered, dried and crystallized in 10 ml of 95% ethanol. Thus, 1 g of 3-benzenesulfonamido-N-[2-(5-dimethylaminomethylfuran-2-ylmethylthio)ethyl]benzamide oxalate is obtained as a vitreous solid.

EXAMPLE 7

To a solution of 2 g of 3-butanesulfonamido-N-[2-(5-dimethylaminomethylfuran-2-ylmethylthio)ethyl]benzamide oxalate in 10 ml of water there is added sodium hydroxide until a strong basic reaction is obtained. The mixture is extracted with a mixture ethyl acetate:ethanol 9:1, the organic phase is dried over anhydrous sodium sulfate and evaporated to dryness. Thus, there is obtained 1.5 g of 3-butanesulfonamido-N-[2-(5-dimethylaminomethylfuran-2-ylmethylthio)ethyl]benzamide as an oily yellowish product.

IR: 3.500, 3.000, 1.640 and 1.148 cm$^{-1}$.

$^1$H NMR Spectrum. (Solvent: DMSO-d$_6$) $\delta$TMS (ppm): 0.83 (3H, m→t), 1.1–1.8 (4H, m), 2.11 (6H, s), 2.63 (2H, m→t), 2.9–3.6 (4H, m), 3.34 (2H, s), 3.75 (2H, s), 6.15 (2H, m), 6.2–6.8 (4H, m), 8.5 (1H, tb, disappears by addition of D$_2$O).

EXAMPLE 8

Tablets comprising one of the products described in Examples 1 to 7, having the following composition:

| Active substance | 100 mg |
|---|---|
| lactose | 70 mg |
| potato starch | 40 mg |
| polyvinylpyrrolidone | 8 mg |
| magnesium stearate | 2 mg |

The mixture of the active substance with the lactose and potato starch is moistened with a 15% alcohol solution of polyvinylpyrrolidone, the granules formed are passed through a 1 mm sieve, mixed with the magnesium stearate and tablets are formed by compression. Weight of a tablet: 220 mg.

EXAMPLE 9

The tablets manufactured as described in Example 8 are coated in known manner by a coating for pills consisting essentially of sugar and talc and the finished pills are polished with beeswax. Weight of a pill: 300 mg.

EXAMPLE 10

Capsules comprising one of the products described in Examples 1 to 7, having the following composition:

| Active substance | 200 mg |
|---|---|
| cornstarch | 90 mg |
| talc | 10 mg |

The active substance and the excipients are intimately mixed and the mixture thus obtained is introduced into capsules of gelatine of dimension 1. Contents of a capsule: 300 mg.

EXAMPLE 11

Suppositories comprising a product as described in Examples 1 to 7, having the following composition:

| Active substance | 300 mg |
|---|---|
| mass for suppositories (Witespol W 45) | 1.450 mg |

The finely pulverized active substance is suspended in the mass for suppositories at 37° C. and the mixture is poured into moulds which are slightly cooled beforehand. Weight of a suppository: 1.750 mg.

EXAMPLE 12

Tablets comprising one of the products described in Examples 1 to 7, having the following composition:

| Active substance | 150 mg |
|---|---|
| microcrystalline cellulose | 75 mg |
| lactose | 100 mg |
| magnesium stearate | 7 mg |
| talc | 18 mg |

The powders are passed through a 0,3 mm sieve, then the ingredients are mixed until a homogeneous mixture is obtained which is compressed and granulated. The granules thus obtained are utilized to form tablets by compression. Weight of a tablet: 350 mg.

EXAMPLE 13

By operating as described in Example 12, tablets comprising one of the products described in Examples 1 to 7, having the following composition:

| Active substance | 350 mg |
|---|---|
| microcrystalline cellulose | 100 mg |
| lactose | 125 mg |
| magnesium stearate | 10 mg |
| talc | 15 mg | are prepared. Weight of a tablet: 600 mg.

EXAMPLE 14

Tablets comprising one of the products described in Examples 1 to 7, having the following composition:

| Active substance | 150 mg |
|---|---|
| microcrystalline cellulose | 75 mg |
| talc | 15 mg |
| polyvinylprrolidone | 30 mg |
| precipitated silica | 25 mg |
| magnesium stearate | 5 mg |

All the ingredients, except the lubricant, are intimately mixed in a mixing machine for 15 minutes, then the mixture is binded by gradual addition of water. The mass is passed through a 1.25 mm sieve. The granules are dried in a fluidized bed dryer until a proper wetness is obtained (about 2% water). To the uniform mass there is added the lubricant and tablets are prepared by compression. Weight of a tablet: 300 mg.

In the same manner, tablets comprising 250 mg of active substance are prepared.

EXAMPLE 15

Coated tablets comprising one of the products described in Examples 1 to 7, having the following composition:

| Active substance | 150 mg |
|---|---|
| carboxymethyl starch | 10 mg |
| microcrystalline cellulose | 85 mg |
| lactose | 135 mg |
| hydrogenated castor-oil | 10 mg |
| magnesium stearate | 5 mg | are prepared by operating as described in Example 14. The tablets thus obtained are coated with a film having the following composition:

| buthyl phtalate | 0.300 mg |
|---|---|
| dimethylaminoethyl butyl polymethacrylate | 1.850 mg |
| polyethyleneglycol 1500 | 0.080 mg |
| precipitated silica | 0.020 mg |
| talc | 0.900 mg |
| titanium dioxide | 1.850 mg | dissolved in a solvent which is eliminated by evaporation in a fluidized bed dryer. Weight of a tablet: 400 mg.

We claim:

1. An amidobenzamide selected from the group consisting of compounds of formula

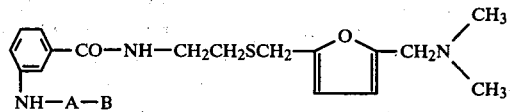

wherein A represents a CO or SO$_2$ group and B represents an alkyl group of from 1 to 6 carbon atoms or a phenyl, pyridyl, pyridyl 1-oxyde, pyrazinyl or thienyl group; or a pharmaceutically acceptable acid addition salt thereof.

2. An amidobenzamide as claimed in claim 1 which is the 3-butanesulfonamido-N-[2-(5-dimethylaminomethylfuran-2-ylmethylthio) ethyl]benzamide or a pharmaceutically acceptable acid addition salt thereof.

3. An amidobenzamide as claimed in claim 1 which is the 3-benzenesulfonamido-N-[2-(5-dimethylaminomethylfuran-2-ylmethylthio) ethyl]benzamide or a pharmaceutically acceptable acid addition salt thereof.

4. An amidobenzamide as claimed in claim 1 which is the 3-(2-thiophenecarboxamido)-N-[2-(5-dimethylaminomethylfuran-2-ylmethylthio)ethyl]benzamide or a pharmaceutically acceptable acid addition salt thereof.

5. A pharmaceutical composition in dosage unit form having histamine H$_2$ receptor blocking properties containing, as active ingredient, an amount of from 10 to 1000 mg, per dosage unit, of an amidobenzamide as claimed in one of claims 1 to 4 in admixture with a pharmaceutical carrier.

6. A pharmaceutical composition as claimed in claim 5 in which the amount of the active ingredient is from 100 to 500 mg per dosage unit.

* * * * *